United States Patent [19]

Sweeney

[11] Patent Number: 4,760,210
[45] Date of Patent: Jul. 26, 1988

[54] PARTIAL OXIDATION SYSTEM

[76] Inventor: Maxwell P. Sweeney, 1817 Fanning St., Los Angeles, Calif. 90026

[21] Appl. No.: 684,806

[22] Filed: Dec. 21, 1984

Related U.S. Application Data

[63] Continuation of Ser. No. 228,909, Jan. 27, 1981, abandoned.

[51] Int. Cl.$^4$ .................. C07C 29/50; C07C 5/48; C07C 41/06
[52] U.S. Cl. .................. 568/910.5; 165/8; 568/697; 568/910; 585/634; 585/656; 585/658; 585/910
[58] Field of Search .............. 585/228, 909, 634, 636, 585/654, 910, 911, 921, 924, 955, 616, 656, 658; 568/910, 910.5

[56] References Cited

U.S. PATENT DOCUMENTS

| | | | |
|---|---|---|---|
| 1,675,029 | 6/1928 | James | 568/910.5 |
| 1,976,790 | 10/1934 | Lewis et al. | 568/910.5 |
| 2,128,909 | 9/1938 | Bludworth | 568/910.5 |
| 2,362,196 | 11/1944 | Frey | 585/658 |
| 2,452,569 | 11/1948 | Houdry | 585/910 |
| 2,579,847 | 12/1951 | Murphy | 568/910.5 |
| 2,609,382 | 9/1952 | Mayland | 585/955 |
| 2,844,452 | 7/1958 | Hasche | 585/634 |
| 2,981,747 | 4/1961 | Lang et al. | 585/658 |
| 3,092,667 | 6/1963 | Murphy | 568/910 |
| 3,563,709 | 2/1971 | Staud et al. | 585/636 |
| 3,705,926 | 12/1972 | Rumpf et al. | 585/636 |
| 3,907,665 | 9/1975 | Winter et al. | 585/634 |

FOREIGN PATENT DOCUMENTS

| | | | |
|---|---|---|---|
| 538572 | 3/1957 | Canada | 585/634 |
| 750 | 1/1973 | Japan | 585/636 |

Primary Examiner—J. E. Evans
Attorney, Agent, or Firm—Albert L. Gabriel

[57] ABSTRACT

Method and apparatus for partial oxidation of hydrocarbonaceous gases, wherein a hydrocarbonaceous gas is preheated, reacted with oxygen, and quenched by means of a rotating matrix comprising glassy ceramic fibers. Such a rotating matrix may be constructed and compartmented by a method and apparatus which utilizes the inherent tensile strength properties of the fibers to provide strength to the compartment walls. Such partial oxidation method and apparatus is especially useful in a direct, integrated process for the production of tert-butyl ethers, wherein the product of partially oxidizing methane and isobutane are caused to be methanol and isobutylene, which intermediates are directly recovered and combined to form methyl tert-butyl ether by method and apparatus of the invention. Furthermore, by-products of such partial oxidation may also be converted to useful tert-butyl ethers.

9 Claims, 2 Drawing Sheets

PARTIAL OXIDATION SYSTEM

This is a continuation, of application Ser. No. 228,909, filed Jan. 27, 1981, now abandoned.

RELATED APPLICATION

This application is being filed concurrently with my application entitled SYNTHESIS GAS SYSTEM, Ser. No. 228,908, the present invention being usable in an embodiment of the invention described and claimed in such related application. A copy of the present application is appended to and incorporated by reference in such related application. Similarly, a copy of such related application is appended hereto and is hereby incorporated by reference as a part of the present application.

BACKGROUND OF THE INVENTION

1. Field of the Invention

The invention is in the field of partial oxidation of hydrocarbonaceous gases.

2. Description of the Prior Art

Partial oxidation processes, both in the gaseous and in the liquid phases, have been known in the art for many years. It has long been known, for example, that methane may be partially oxidized to formaldehyde at low pressures (near atmospheric pressure), and that a substantial conversion of methane to methanol, as well as formaldehyde, occurs at elevated pressures, usually between about 50 and about 200 atmospheres. Some of the more successful experiments at elevated pressures were performed by E. H. Boomer and V. Thomas, *Canadian Journal of Research*, Vol. 15, Sec. b, 414–433 (1938), using 3%–7% of oxygen in methane at 475° C. and 140–220 atmospheres. They investigated the effect of various parameters, including "catalytic" effects of various solids; and they concluded (p. 433) that "the conversion of total carbon in the system to methanol is very low, and probably not of commercial value even in a circulatory system."

In view, however, of the apparent simplicity of the process, and the large availability of natural gas at relatively high pressure, there have been numerous experiments and even attempts to commercialize the partial oxidation of methane, but none has heretofore been successful. Except for the gas/catalytic oxydehydrogenation of normal butylenes to butadiene, and some early gas phase partial oxidation of propane and butane, the more commercially successful partial oxidations, particularly of alkanes, have been in the liquid phase, at relatively low temperatures, as very recently summarized by J. E. Lyons, *Hydrocarbon Processing*, Nov. 1980, 107–119.

Even in the case of low pressure partial oxidation of methane to formaldehyde there has, to applicant's knowledge, been no commercialization, at least in Western countries. The primary reasons for this surprising lack of success have been the relatively low yields, and the complex mixture of products and contaminants produced, especially in the case of partial oxidation of higher alkanes. Low yields result from the fact that the desired partial oxidation products are much more readily further oxidixed to undesired carbon monoxide, carbon dioxide and water than is the parent hydrocarbon, and this adverse factor is especially the case with methane—much the hardest to react of all hydrocarbons. Thus, the only very high ratios of hydrocarbon to oxygen can increase the probability of the desired, as compared to the undesired, reactions occurring. And, in consequenoe, very low yields per pass occur.

Furthermore, as Boomer and Thomas report, the presence of ordinary materials of commercial construction, especially steel and its alloys, has an erratic and adverse effect upon yields. While copper and silver materials of construction provided good means for heating the charge, they tended to promote further oxidation of the desired methanol to undesired formaldehyde and formic acid. Furthermore, since water vapor is also a substantial product of the reaction, it is necessary to separate the products from water, which is notoriously difficult in the case of formaldehyde and formic acid, and particularly so in the presence of methanol—which forms hemiacetals and acetals with formaldehyde and methyl formate with formic acid, both sets of reactions being catalyzed by formic acid itself.

Still other problems involve preheating, maintaining and controlling the reaction temperature, and usefully recovering the substantial heat produced by the partial oxidation reaction, particularly since very large amounts of gases must be heated and reacted in comparison to the amount of product produced.

SUMMARY OF THE INVENTION

In view of these and other problems in the art, it is a general object of the present invention to provide a novel method and apparatus for the partial oxidation of hydrocarbonaceous materials in the gas phase, wherein the ultimate yield of desired partially oxidized products is maximized.

It is another object of the invention to provide a novel system for preheating, reacting, quenching and cooling, usefully recovering heat, and recovering desired products, wherein nondeleterious materials of construction are caused to accomplish these steps.

In direct contrast to the experience of the prior art, it is another object of the invention to provide a commercially practicable means for partially oxidizing methane and recovering in maximum ultimate yield methanol, wherein the undesired partial oxidization products are at least in part recycled, thereby both contributing to the yield of methanol and stabilizing the reaction system.

Another general object of the invention is to provide a system for partial oxidation wherein the yield of alcohols is maximized relative to the yield of aldehydes and acids, wherein pressures greater than about 20 atmospheres are practicably utilized, premature reaction is inhibited, short reactions times (less than about 1 second) are practicable, and the reacted mixture—in large volumes—is rapidly quenched.

Another object of the invention is to provide an economical means, by partial oxidation of hydrocarbons higher than methane, for the production of olefins in high yield, wherein oxygen and its reaction intermediates efficiently removes hydrogen atoms from the hydrocarbon precursor to the olefin, and wherein pyrolysis to products of lower carbon atoms is minimized.

Another object of the invention is to provide a highly economical means for simultaneously in the same equipment producing and then combining carbinols and isobutylene to form tert-butyl ethers, wherein the ultimate yield of each of these intermediates from its precursor is enhanced relative to its production separately.

According to the invention, a mixture comprising hydrocarbonaceous gases and oxygen is rapidly preheated by heat exchange with product gases from the partial oxidation reaction, then allowed to react under controlled conditions, and finally quenched by again passing rapidly in heat exchange.

In preferred aspects, the mol ratio of hydrocarbon to oxygen is maintained above about 8 and the heat exchanger is a compartmented, radial flow rotary regenerator, the matrix of which is comprised of inert fibers of ceramic in glassy form, which inhibit undesired reactions during preheat and quench. The reaction space is preferably size-controllable and the speed of rotation of the regenerator is varied to control the preheat of the reactant gases.

According to the invention, the annular matrix of the regenerator is readily fabricated, compartmented and strengthened by winding glassy ceramic cloth on a core and forming a line of ceramic cement across the face, rotating the core by a fraction of a revolution, and repeating.

In a preferred aspect of the invention, the rotating matrix is fitted with inner and outer rotating plenum means for distribution of the gases across the face of the matrix and collecting the gases therefrom, and leakage of reactant gases into product gas is minimized by providing seal shoes which are self-adjusting towards the containing walls of the plenum, by causing each shoe to move toward the cooperating wall under the action of a biasing force, while a small clearance is maintained between the shoe and the wall by injecting a small flow of a relatively high pressure fluid between them.

The configuration of the increments of reactant gas entering the reaction space in the preferred embodiment is such that homogeneity of reaction is obtained, by providing a sufficient induction time and temperature for the first increment while later, less preheated, increments are "seeded" with free radicals by the first increment, and, at the same time, the first increment is prevented in overshooting in temperature by the later, cooler increments admixed therewith. This preferred configuration also permits advantageously short residence times for the bulk reaction, while providing sufficient induction time for the generation of the necessary free radicals which cause the partial oxidation. Accordingly, the partial oxidation reaction is stabilized at the optimum conditions.

The means provided is thus a preferred means for the synthesis of methanol from methane and isobutylene from isobutane and then for the novel direct synthesis of both components of the relatively new and valuable antiknock replacement for lead in gasoline, methyl tert-butyl ether. According to the invention, methyl tert-butyl ether is directly synthesized from methane and isobutane by simultaneous partial oxidation to methanol and isobutylene, respectively; removal of water from the reaction gas; and then combination of them over an acid-reacting solid catalyst.

Further objects and advantages of the present invention will appear during the course of the following part of the specification, wherein the details of construction, the mode of operation and novel method steps of presently preferred embodiments are described with reference to the accompanying drawings, in which:

DETAILED DESCRIPTION

The Metherox Process

Figure 1:
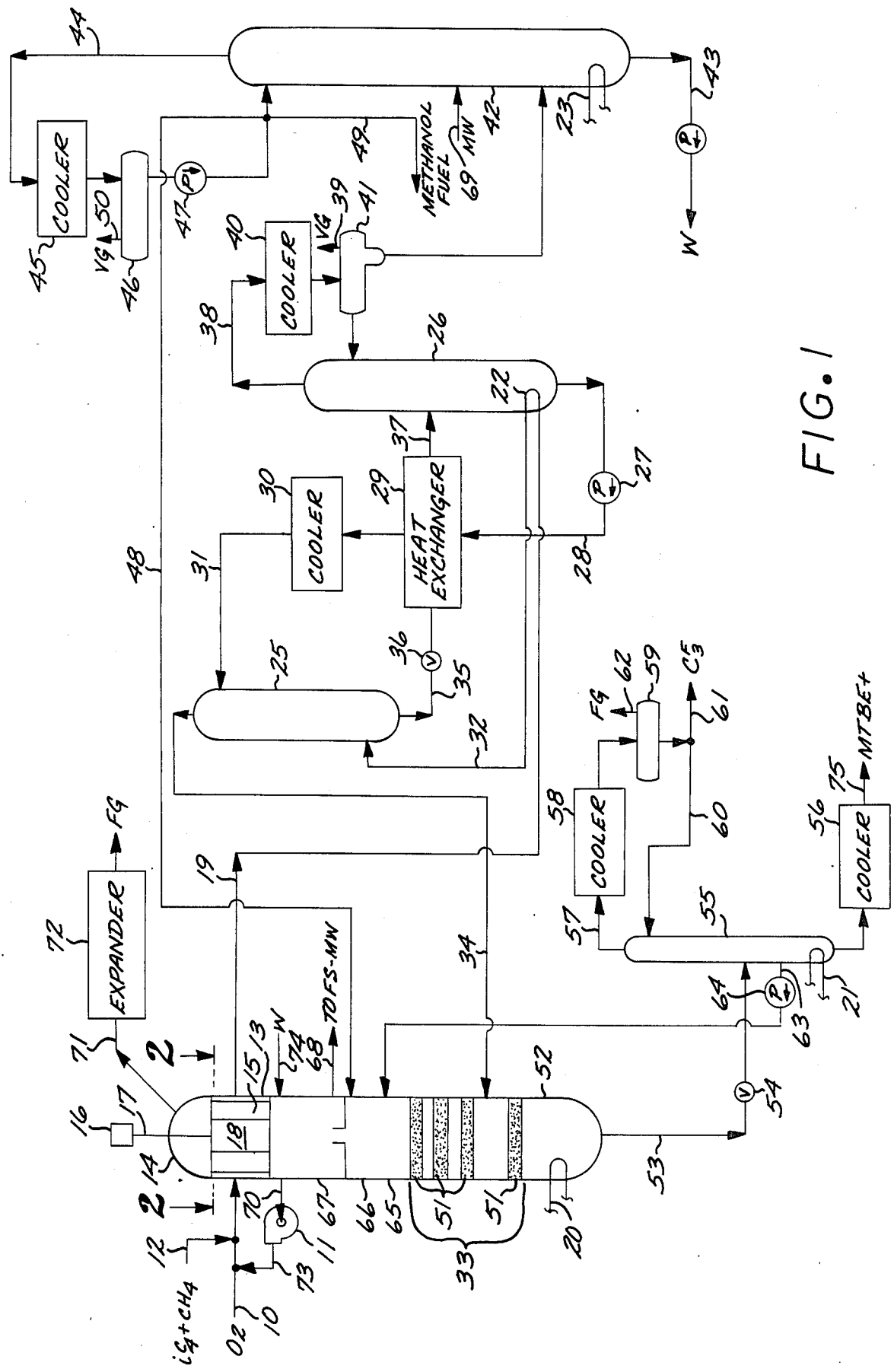
FIG. 1 is a schematic diagram illustrating the preferred method and apparatus of the invention for producing and then combining carbinols and isobutylene to produce tert-butyl-ethers, sometimes referred to hereinafter as the "Metherox" process.

FIG. 1 illustrates diagrammatically the preferred steps of a preferred embodiment utilizing the invention. Preferably relatively pure oxygen in line 10—compressed to at least reaction pressure, which is preferably between about 20 and about 200 atmospheres absolute (ata), and usually between about 50 and about 100 ata—is mixed with recycle gas delivered by blower 11 and fresh hydrocarbonaceous feed in line 12. If only methanol product is desired this feed would comprise methane (and for higher alcohols, the corresponding hydrocarbon). If the desired product is tert-butyl ether, isobutane is fed along with methane. As will be further seen below, the reaction mixture in the latter case comprises both a relatively high ratio of hydrocarbon to oxygen (always beyond the rich explosive limit, preferably greater than 4, and more preferably greater than about 8, and for economic reasons, less than about 40, mols of hydrocarbon per mol of oxygen); and a relatively high ratio of methane to isobutane, again preferably greater than 4, and more preferably greater than about 8 mols of methane per mol of isobutane.

In the heat exchanger-reaction section 13 of vessel 14, the reaction mixture is preheated, preferably by the rotating ceramic fiber matrix 15, which is rotated by motor 6 and shaft 17 at between about 1 and about 20 revolutions per minute (RPM), and usually between about 5 and about 15 RPM. The matrix is preferably compartmented and constructed as described by reference to FIG. 3, preferably comprising inert inorganic oxides combined in a glassy form and woven into a cloth from continuous filaments. The precise composition of the ceramic is not critical to the desired reaction (provided that it is commercially "low" in easily reducible oxides such as those of iron) and thus can be selected from materials generally available commercially, based upon the necessary temperature resistance required. There are many advantageous uses for such rotary heat exchangers, since they very compactly contain a very large surface area for heat transfer into and out of the matrix itself acting as a heat storage medium, since they are inert and non-reactive to nearly all atmospheres, since they are relatively light in weight and inherently self-insulating, and since such glassy ceramic fibers are quite typically very strong. In general the more temperature-resistant is the fiber the more costly. Thus, for uses below about 350° C.–400° C. (662° F.–752° F.) ordinary grades of glass fiber cloth will suffice. And, for example up to about 1000° C. (1832° F.) it is said that a high silica fiber product ("Refrasil")

of the Hitco Division of Armco is suitable and available, and their chrome-impregnated silica fiber to about 1260° C. (2300° F.); and it is said that a product of the 3M Company ("Nextel") is suitable and available for use up to about 1420° C. (2588° F.). This latter product is said to hold 90% of its room temperature tensile strength (250,000 psi) to 1093° C. (2000° F.), and to comprise 62% $Al_2O_3$, 24% $SiO_2$ and 14% $B_2O_3$.

In the subject embodiment of the invention, material such as "Refrasil" will be quite adequate, since the preferred reaction outlet temperature is preferably between about 450° C. and about 700° C., more preferably between about 550° C. and about 650° C., and the preheat temperature is preferably between about 425° C. and about 600° C., and will usually average between about 475° C. and about 550° C.

During the preheating of the mixture to be reacted, it will be seen that the mixture comes in contact with no (deleterious) metals, and that the very large surface area per unit volume inhibits any deleterious reactions. These considerations are crucial, since reaction on metal surfaces is known to cause over-oxidation of the reactant, and substantial reaction at less than the desired temperature more preferentially oxidizes the desired intermediates relative to the parent hydrocarbon, especially in the case of methane. As described below in reference to FIG. 2, not only is the preheat and reaction temperature readily controllable by the preferred means described, but also the reaction space itself—i.e., the residence time—is controllable independent of flow rate. This latter is important because the optimum reaction temperature is the highest that causes the reaction to be just nearly completed in the shortest time which can be physically and practicably provided. This conclusion results from the fact that the activation energy for free radical attack on methane is higher than for such attack on the desired methanol product; thus, the higher the temperature the closer together are the rates. An important advantage of the preferred preheat/reaction means, therefore, is that it lends itself to relatively very short residence times; i.e., less than about one second, and preferably less than about 0.5 second.

In the preferred embodiment of the Metherox process, preferably as illustrated in FIG. 1, most of the methane reacts according to the overall reaction: $CH_4 + 1/2 O_2 = CH_3OH$, and most of the isobutane reacts accordingly to the overall reaction: $iC_4H_{10} + 1/2 O_2 = iC_4H_8 + H_2O$. Each of these overall reactions is the end result of a very complex series of free radical reactions. Free radicals are produced of varying activity; thus, towards the various substrate molecules, quite generally the order in decreasing activity is: $\cdot OH > CH_3O \cdot > CH_3 \gg HO_2 \cdot > CH_3OO \cdot$. When methane is partially oxidized by itself, the latter, peroxy, radicals are quite inactive toward methane, and in consequence build up in concentration, attack the products methanol and formaldehyde, and parasitically combine together and generally lower yields.

In respect to the substrates, their activity towards hydrogen atom abstraction by any given free radical quite generally and substantially increases in the order $CH_4 <$ primary H [e.g., $C_2H_6$] $<$ secondary H [e.g., $(CH_3)_2CH_2$] $<$ tertiary H [e.g., $(CH_3)_3CH$]. It is now important to realize that the prior order of decreasing free radical activity is also an order of increasing free radical selectivity. Thus while the peroxy radicals react poorly with methane, they very selectively remove the weakest hydrogen atom from other substrates, and most preferably tertiary hydrogens; whereas the other free radicals listed are relatively unselective, and especially hydroxyl. Because in isobutane there are 9 primary hydrogens and only one tertiary, the unselective radicals tend to remove a primary hydrogen.

Now it is known that in partial oxidations that the tertiary radical, $(CH_3)_3C\cdot$, passes by the reaction: $(CH_3)_3C\cdot + O_2 = (CH_3)_2C=CH_2 + HO_2$ virtually quantitatively to isobutylene; while in the case of the isobutyl radical (formed by removal of a primary hydrogen from isobutane), only some 50% passes to isobutylene, and the rest undergoes a complex series of undesirable side reactions.

It is therefore now seen that the selective free radicals are highly desirable in reacting with isobutane; for example, according to the reaction: $(CH_3)_3CH + HO_2 \cdot = (CH_3)_3C \cdot + HOOH$. However, the product HOOH under partial oxidation conditions breaks down according to the reaction: $HOOH = 2 \cdot OH$, yielding the very unselective hydroxyl radicals. In isobutane partial oxidation by itself, these will cause the formation of substantial amounts of the undesired isobutyl radical, thereby lowering the yield of the desired isobutylene. However, with a high proportion of methane present, it is now seen that it will be (desirably) attacked by these hydroxyls, ultimately, under the preferred conditions, yielding a high proportion of the desired methanol. Thus, by conducting a combined partial oxidation, the yields of both methanol and isobutylene from their respective precursors will be appreciably enhanced! Especially today and in the future, these increased yields from increasingly expensive fossil fuels will be economically very important.

Still, in addition to these desired products, there are produced some byproducts, comprising mainly formaldehyde, isobutylene oxide, isobutanol, propylene, and carbon monoxide, as well as water. And in order that the Metherox process make proper provision in respect thereto, it is necessary to consider their presence and fate in subsequent processing steps, as described below.

After reaction in reaction zone 18 the product gases pass back through another portion of matrix 15. During reaction the temperature of the gases increases substantially due to the exothermic nature of the reaction so that then the gases are hotter than the solids in the matrix, and serve to heat it as they are being cooled. Thus is a temperature gradient established in matrix 15. And thus this quench rate, generally of over 1000° C./second, combined with the large surface area, effectively quenches the secondary, undesired reactions.

Heat is further usefully recovered from these gases in line 19 by their serving to provide heat in necessary reboil duty in other steps in the process, as indicated by heat exchange loops 20, 21, 22, 23 (supplemented where or if necessary by steam or other hot media). During this further cooling, water vapor and some methanol will generally condense, further recovering (latent) heat.

Inasmuch as the preferred well known commercial catalyst for conducting the combination reaction: $CH_3OH + (CH_3)_2C=CH_2 = CH_3OC(CH_3)_3$ (methyl tert-butyl ether), is a strongly acid-reacting solid catalyst, such as the "Amberlite" macroreticular ion exchange catalyst (in the hydrogen form) product of Rohm and Haas, which is strongly deactivated by water, it is necessary to virtually completely remove water from the reaction product gases in line 32. This removal is most readily and preferably accomplished by novel means, wherein other products of the reaction are recycled and utilized as dehydrating absorbents.

Thus, it will be found that, under the preferred conditions prevailing in dehydrator vessel 25 and water stripper vessel 26, the formaldehyde byproduct will, to a large extent, combine with the isobutyl alcohol byproduct to form a hemiacetal, according to the reaction: $CH_2O+iC_4H_9OH=(CH_3)_2CHCH_2OCH_2OH$. This material will build up in concentration in these vessels because its vapor pressure will be low relative to that of other components, and it will serve as a good absorbent for water. Thus, having been stripped of water in vessel 26, it will be returned, through pump 27, line 28, heat exchanger 29, cooler 30 and line 31 to the top of vessel 25. The temperature at the top of vessel 25 may be adjusted so that the net make of the various products and byproducts, comprising formaldehyde and isobutanol, is carried overhead into line 34, along with the gases introduced to vessel 25 via line 32; or alternatively a small liquid stream (not shown) may be taken from line 31 and passed directly to the catalytic reaction zone 33 of vessel 14; or, if desired, this minor product may be separately removed from the system.

Preferably a substantial portion of the methanol product will also pass overhead as vapor in line 34, while essentially all of the water vapor in the gases in line 32 is absorbed therefrom by the (dried) liquid entering vessel 25 via line 31. This water-enriched liquid will then pass via line 35, backpressure valve 36, exchanger 29, and line 37 to water stripper vessel 26. The overhead from this stripper in line 38 will comprise a complex mixture, including some fixed gases which are vented via line 39 after condenser 40 and separator 41. Depending upon exact reaction and operating conditions, the liquid phase from condenser 40 will probably split into two phases, which is preferred. If not, a relatively very small amount of hydrocarbonaceous material, preferably that which is valuable in the final product, such as natural gasoline, naphtha, benzene, or toluene, added to the vapor in line 38 (or other adjacent convenient point) will suffice to cause this separation into two liquid phases. Since the hydrocarbonaceous phase is completely refluxed to the top of vessel 26, the added material, if any, almost entirely returning back overhead, very little makeup of such material will be required. The aqueous phase from separator 41 is passed to fractionator-stripper vessel 42, and comprises methanol and water. From the bottom of vessel 42 the stream 43 comprising water is removed, while a methanol fuel stream is produced from the overhead vapors in line 44, via condenser 45, separator 46 and pump 47. Depending upon the production of methanol and other carbinols relative to that of isobutylene, all or part of this methanol may be required within the process to produce tert-butyl ethers. This requirement is recycled via line 48, with the excess production being removed via line 49. Some gases also vent via line 50.

The novel preferred system of the invention for reacting methanol and other carbinols with isobutylene to form tert-butyl ethers as described below uniquely overcomes some otherwise serious problems with this combination reaction. In state-of-the-art systems for performing this reaction all the methanol required, including recycle, and the isobutylene (in its liquid feed mixture)—often along with some recycled tert-butyl ether—flows together over the catalyst. But the reaction is inhibited by high methanol concentrations—which methanol is preferentially imbibed by the catalyst to the exclusion of isobutylene therefrom. Also the reaction is exothermic and limited by equilibrium. Thus, commonly the reaction is first inhibited by high methanol content and then, through heat release as well as tert-butyl ether formation, by equilibrium. Both the methanol concentration profile and the temperature profile during reaction thus tend to be just opposite to that desired, necessitating excessive catalyst requirements and elaborate heat exchange requirements with cooling water.

In the preferred embodiment of the present invention, by performing the combination reaction in the presence of a countercurrently-flowing heat-carrying gas, the elaborate cooling provisions are eliminated; i.e., the entering gas can be already cooled to any desired temperature, thus cooling the tert-butyl ether product towards the end of its reaction, when it would conventionally be most limited by equilibrium. And, as will be seen, the preferred embodiment readily provides for recycle to the reaction zone of both isobutylene and methanol contained in the crude tert-butyl ether stream, so that equilibrium problems are obviated.

Thus, the gases containing isobutylene and some of the product methanol entering vessel 14 via line 34 are met by downflowing liquid comprising methanol, tert-butyl ethers, and some dissolved isobutylene. The liquid absorbs isobutylene from the upflowing gas in zone 33 of vessel 14, and its favorable temperature—preferably about 40° C.–90° C. and more preferably about 50° C.–70° C.—and ratio to methanol enhances its reaction rate within the pores of the catalyst, preferably arranged in packed sections 51 above and below line 34.

Because of their lower volatility relative to other components the first carbinols to accumulate in the liquid near the junction of line 34 are isobutyl alcohol and its hemiacetal referred to above. They react within the catalyst with isobutylene to form isobutyl tert-butyl ether (TBE) and isobutoxymethyl TBE, respectively. The byproduct oxides, mainly isobutylene oxide, also react within the catalyst in the presence of methanol first to form a glycol ether, and then, in the presence of isobutylene, to form methoxyisobutyl TBE.

The principal use of TBE's is as a valuable antiknock in gasoline, which in the optimum 7%–10% level therein not only replaces lead antiknock compounds, but also extends the volume of gasoline, utilizing natural gas components rather than increasingly costly petroleum oil. And it is to be expected that these byproduct TBE's will have comparably high blending octane values to that of the methyl analog, MTBE, and thus be approximately equally valuable (per mol of TBE). (At the same time they may, however, require a somewhat greater amount of anti-oxidant gum-inhibitor additive).

The downflowing crude tert-butyl ether product from packed sections 51 then preferably enters stripping section 52 where dissolved fixed gases are stripped therefrom, passes through line 53 and backpressure valve 54 to stabilizer vessel 55 where components boiling lower than methyl tertbutyl ether (MTBE) are at least in part stripped therefrom, to control vapor pressure of the product. After cooling in cooler 56, the product comprising tert-butyl ethers is removed via line 75.

In the presence of high concentrations of tert-butyl ethers, methanol, as well as isobutylene and lighter, is more volatile than MTBE. These will, therefore not tend to pass out in line 75, but rather will accumulate within vessel 55, particularly since the predominant component in line 57, condensed in condenser 58, passing as liquid into separator 59 and refluxed to vessel 55 via line 60, is propylene. The net production of this stream may either be taken as a separate, valuable product via line 61, or by adjusting temperatures and pressures be taken as a gas via line 62, which itself may be utilized as fuel gas to power, for example, a gas turbine or to raise or vaporize steam, in order to provide the oxygen and heat requirements for the process. Vent gases previously mentioned are advantageously similarly used.

Inasmuch as unreacted methanol and isobutylene, as well as MTBE, accumulates within the middle section of vessel 55, this mixture is taken via sidedraw 63 and pump 64 and recycled to vessel 14 above absorber section 65 of vessel 14, in which residual isobutylene is absorbed from the gases passing therethrough. MTBE which vaporizes into these gases is absorbed in absorber section 66 by methanol entering via line 48, and methanol in these gases is preferably absorbed by water (preferably recycled from stream 43) introduced via line 74 into absorber section 67. The methanol/water mixture resulting is collected and removed via line 68, and preferably returned for fractionation to vessel 42, entering via line 69.

The offgases from section 67 preferably enter blower 1 via line 70, and most of the gases therefrom are recycled to the partial oxidation reaction. The excess accumulation of gases, comprising byproduct carbon monoxide as well as residual methane, is preferably taken from the discharge of blower 11 in line 73, and passed separately by a line not shown and separately enters matrix 15, where it is preheated, thereby recovering relatively high temperature heat therefrom, and leaves matrix 15 and vessel 14 via separate passages and line 71. This preheated offgas is preferably furnished to an expander 72 to recover useful energy, and may then serve to augment fuel gas or utilized in other well-known ways to recover its valuable components.

Reqenerative Preheat/Reactor

Figure 2:
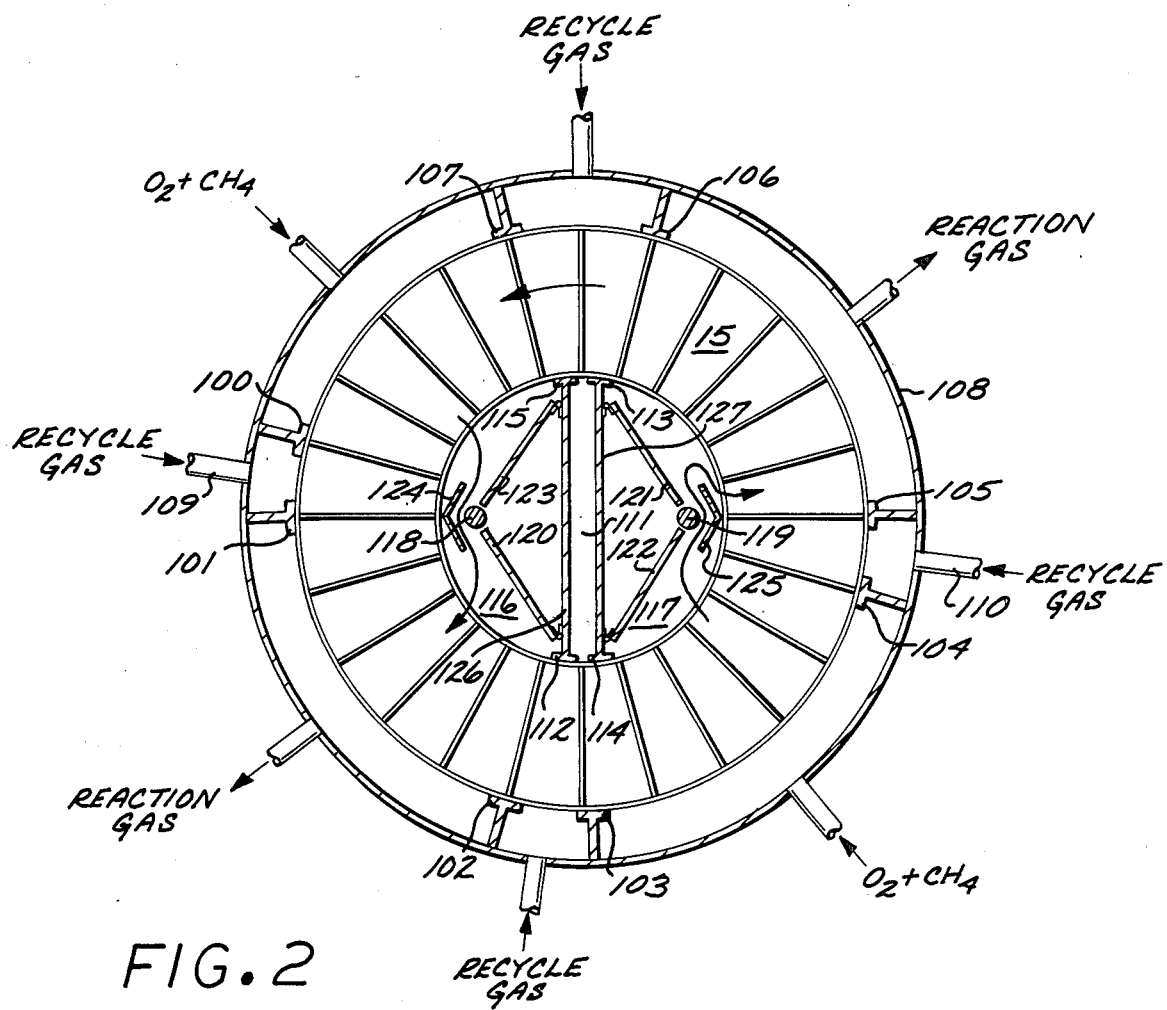
FIG. 2 is a diagrammatic view in plan of a horizontal section of the preferred, rotary heat exchanger-reactor of the invention, sometimes referred to hereinafter as a "methanoxer", in which the reactant gases are quickly preheated, reacted, and quenched and cooled.

Referring to FIG. 2, which schematically shows in enlarged horizontal sectional view the preferred arrangement of heat exchanger/reactor 13, it is preferred that the various flows be symmetrical about the centerline. In this way, rotating matrix 15 is in pressure balance, inasmuch as while the only pressure differences are due to pressure drops caused by flow therethrough—in contrast to other uses of rotary heat exchangers, such as in gas turbine regenerators—still such differences exerted over substantial areas may unduly cause operational problems. Such symmetrical flows are accomplished by providing the matrix 15 with an annular arrangement of uniformly sized radial compartments 15a separated from adjacent compartments 15a by radial walls 15b that may be made of ceramic cement as described below.

The outer seal shoes 100, 101, 102, 103, 104, 105, 106 and 107 may be separate structures mounted on the vessel wall 108 as shown, or they may be combined together in a pair of shoes opposing each other within which the entering gases are fed to the appropriate sections of matrix 15, as more fully described in my co-pending application Ser. No. 228,908, the open spaces between the pair of shoes then serving as exit plenums.

Because it will quite generally be preferred that oxygen-containing gas not leak or be carried over within a matrix compartment into the reaction offgas plenums, it is preferred that recycle gas (not containing oxygen) to flush out (inwards) oxygen-containing gas be introduced,—via lines 109 and 110—to that compartment which is just before the flow within the matrix reverses, and commences flowing outward. For similar reasons, i.e., to not "waste" substantial product-containing reaction offgases into gases which are removed from the system via plenum 111, recycle gas is preferably introduced into that matrix compartment which is just about to switch back to inward flow prior to its closing at the inner fixed shoes 112 and 113. Thus the recycle gas first backflushes reacted gas back through the matrix, thereby causing such reacted gas to tend to exit via a prior compartment; and then this backflushing gas feeds to plenum 111 as the particular compartment reaches the openings between seal shoes 112 and 114 and between shoes 113 and 115.

In startup operation, in order to establish a temperature gradient in matrix 15 such that feed is sufficiently preheated so that partial oxidation can commence, the inner plenums 116 and 117 must be heated. However, because the heat exchange efficiency of the rotating matrix 15 is intrinsically very high, especially at the substantially reduced flow rates preferred for startup, relatively little heat will be required since it will be almost completely recovered by being stored within the inner portions of matrix 15. Thus while an auxiliary heater or other means can be employed, it is preferred that electrical, resistance-heated startup rods 118 and 119 be employed. The hot surface of these rods will relatively quickly initiate partial oxidation, the heat release from which will perform most of the heating; also these hot rods will stabilize the oxidation before final operating temperatures are reached, as flow rates are increased.

During this warmup phase, it is to be emphasized that a substantial induction period of time, of the order of several seconds, during which free radical concentrations are building up will occur along the reaction path of the reactant gases in plenums 116 and 117 and it is preferred that the residence time for the reaction be at a maximum, both because of reduced flow rates, and because of reaction space available.

Thus, residence time control baffles 120 through 123, which are preferably hinged to inner shoes 112 through 115, respectively, are preferably drawn back against plates 126 and 127 containing plenum 111, thereby maximizing the reaction space available in plenums 116 and 117. And as previously explained, once final reaction temperature is attained, it is preferred that active residence time, i.e., the residence time for the bulk of the reacting gas, be held at a minimum, consistent with economic considerations of pressure drops and the like and the necessity of providing for the necessary induction period. Reduction of residence space is preferably accomplished by rotating the baffles 120 through 123 into a position similar to that shown, such that most of the residence space is rendered inactive, and the bulk of the gases first pass inward through the sections of the matrix between shoes 100 and 107 and between shoes 103 and 104, thereby being rapidly preheated, preferably build up in radical concentration in the space prior to the startup rods, and just complete their reaction (i.e., utilize substantially all of the oxygen available) before then being removed from the reaction zone by passing outward through the sections of matrix 15 radially between shoes 101 and 102, and between shoes 105 and 106. In order that substantially all of the gas react, and not "short-circuit" into and out of the reaction zone, it is preferred that fixed baffles 124 and 125 be installed such that they first direct the last of the preheated gas into mixing in the active zone of free radical buildup just prior to the startup rods, and as shown require such gas to have at least a minimum of reaction residence time before being quenched by passing back into matrix 15.

It is to be emphasized that this form of preheat-reactor-quench system has unique advantages. First, it provides great stability to exothermic reaction systems and provides substantially more "isothermal" reaction kinetics than common exothermic reaction systems. Second, it combines the desirable features of plug flow with those of "cold shot" admixture and with those of backmixing. Third, it provides a wide flow path for preheat but a narrow, relatively high flow rate zone for reaction and a relatively very short reaction space. Fourth, it is self-insulating and inherently very compact. Fifth, it provides a means of preheating and quenching in which deleterious surface reactions are avoided by utilizing an inert, non-catalytic, relatively non-reducible or oxidizable heat transfer medium.

Many of the above features are now readily seen, and apply and are equally advantageous to the performance of endothermic reactions (in which the matrix is preferably cyclically heated by an exothermic reaction prior to the desired endothermic reaction, such as for example, pyrolysis); however, the first two advantages above cited require further explanation.

In respect to stability, it is for example common-place that both oxygen and combustibles may be present together without appreciable reaction, that to be self-sustaining the heat release from a reaction must be greater than the sensible heat required to bring the reactants to reaction temperature; furthermore that there is a highly temperature-sensitive induction period; and that it is quite possible to "blow out" even a flame, let alone a non-flame partial oxidation.

Now it will be seen that in the course of, say, counterclockwise rotation of matrix 15 the hot reacted outflowing gas continues to heat matrix 15 towards its temperature, and that matrix 15 will be at its hottest temperature just before it switches to inflow. Thus, the first inflow, i.e., excess recycle gas taken as hot offgas through plenum 111, will be preheated to the maximum possible temperature. Thus is heat usefully recovered for use elsewhere at the highest possible temperature. But the main point here is that the first of the next inflowing gas is also heated to a relatively high temperature. This gas then relatively quickly builds up in the necessary free radical concentrations to effectuate the desired partial oxidation. However, starting at a relatively high temperature, this first increment of reaction gas would by its heat release during reaction tend to overshoot in respect to the desired reaction temperature. But now, in this preferred configuration, before most of the heat release, it is joined by and mixed with a second increment of gas which has been preheated to a somewhat lower temperature, thereby tending to prevent the first increment from overshooting in temperature. At the same time, by this means, the second increment is "seeded" with free radicals from the first, so that its otherwise relatively long induction period is shortened. And so forth, through each of the incremental additions of reactant gas.

Commonly in exothermic reactions, such as, for example, burners, stability is provided by backmixing. However, if a reaction zone is highly backmixed two undesirable features occur. First, some of the relatively unreacted gas "mixes" itself relatively immediately to the outlet, with relatively little of the desired conversion. And second, some of the gases after reaction are "mixed" around and around and have excessive residence times, which tend to destroy desired products.

In contrast, it is now seen that the present invention achieves stability by the relatively long residence time of the early, hotter increments without "short-circuiting" any increments, and without "overtreating" any increments. The early, hotter increments are not "overtreated" because until free radical concentrations have built up in them very little bulk conversion is occurring; thus desired converted products are not substantially present, and thus are not appreciably undergoing parasitic loss.

Thus it can now be seen that, in spite of wide variations in the reactivity of various feed mixtures, with proper adjustment of design and operating variables of oxygen level in reactants, average preheat temperature, speed of rotation of matrix 15, and position of control baffles 120 through 123, the effective bulk reaction zone—as distinguished from the induction zone—may readily be optimized to a relatively very short distance, amounting to about one-fourth of the total reaction path length. As previously emphasized in reference to FIG. 1, a very small bulk residence time is important in order to maximize yields from such exothermic reactions where the desired products are inherently more readily attacked than is the reactant precursor.

Matrix Fabrication

Figures 3, 4:
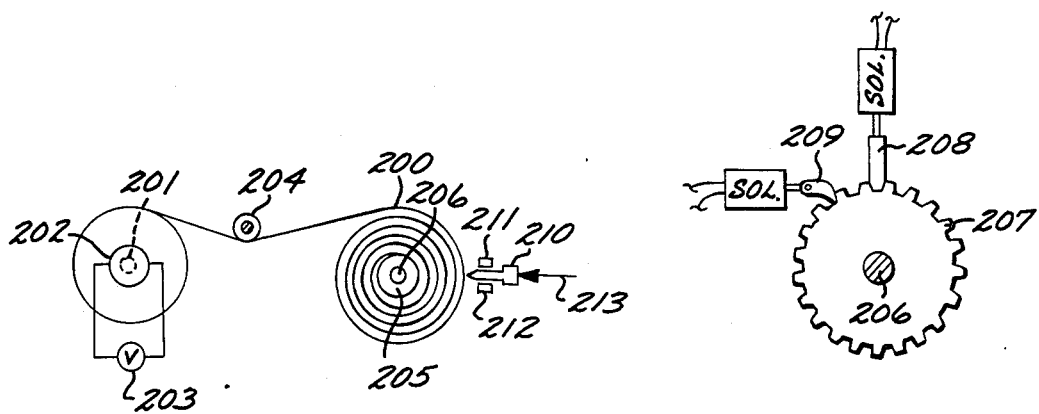
FIG. 3 is a diagrammatic side elevational view illustrating the preferred method of the invention for constructing and compartmenting the preferred ceramic fiber rotary heat exchange matrix of the methanoxer.
FIG. 4 is a diagrammatic side elevational view illustrating an indexing system for stepped rotational movement in FIG. 3.

By reference to FIG. 3 and FIG. 4, it is shown how it is preferred to fabricate matrix 15, to compartment it and to seal its top and bottom extremities. As mentioned in reference to FIG. 1, it is preferred that the matrix be fabricated from cloth; cloth of selected porosity and thread size woven preferably from continuous filament yarn of glassy ceramic composition.

A spool of continuous cloth 200 is mounted upon a spindle shaft 201 fitted with a friction-restraining device. Preferably and conveniently this restraining device is a small, fixed hydraulic, oil-filled motor 202, the shaft of which is attached to shaft 201, with the oil feed and discharge of motor 202 connected together through valve 203. Thus when tension is exerted upon the end of cloth 200, the spool will turn motor 202, and will unwind slowly, at a rate dependent upon the setting of valve 203. Cloth 200 passes under idler roll 204, suitably supported (not shown) so that rotational and vertical, but not significant horizontal, motion is permitted. This idler roll by its weight provides relatively constant tension on the cloth, in spite of intermittent motion downstream from it. Of course, it will be understood by those skilled in such art that valve 203 may be readily controlled by the vertical position of idler roll 204, thereby holding the position of roll 204 within closely defined limits, and in turn holding the tension on cloth 200 virtually constant.

The free end of cloth 200 is temporarily attached to a removable mandrel or held by a permanent core 205 (used in the final matrix to collect gases at the inner periphery of matrix 15) mounted on shaft 206. Also attached to shaft 206 is indexing device 207 shown in FIG. 4, which has a number of circumferential positions equal to the number of radial compartments into which it is desired to divide matrix 15. Cooperating with device 207 are, solenoid or preferably compressed air piston-operated, stop device 208 and, solenoid or preferably compressed air piston-operated, ratchet device 209.

Preferably held on the horizontal plane of shaft 206 by runners 211 and 212 (and directed towards shaft 206) is ceramic cement application "gun" 210 and its carriage (not shown) which is slidably attached to runners 211 and 212, and is preferably actuated in back and forth motion along runners 211 and 212 by a compressed air piston (not shown), or other suitable means, such as a reversing motor and attached drum driving an endless cable over pulleys located beyond either extremity of the desired traverse.

Preferably runners 211 and 212 together with associated equipment are also mounted upon a carriage (not shown) which may be manually or automatically adjusted horizontally to maintain a desired relationship with the face of accumulating cloth 200 upon core 205.

The "gun" carriage mounted upon runners 211 and 212 is also preferably fitted with a small compressed air piston (not shown) actuated such that when, at the end of its travel along runners 211 and 212, gun 210 is momentarily vertically tilted through a fixed arc and then returned to its horizontal position. This projected arc is at least equal to the distance between adjacent compartment barriers or walls 15b. (Alternatively, of course, additional guns may be mounted to apply ceramic cement circumferentially to the extremities of the matrix, rotational increment by increment. However, as will be seen, if such guns flow continuously an undue buildup of cement will occur between increments of rotation, and if flow is caused to be intermittent, occurring only as shaft 206 is indexed, risk of partial stoppage of the preferred relatively quick-setting ceramic cement may occur before flow is resumed, possibly leading to an imperfectly sealed matrix).

In operation, the sequence—controlled by appropriate limit switches (connected to solenoid valves if air operated)—is as follows. Gun 210, fed through line 213 by pressurizing means with ceramic cement, applies a line of cement horizontally across the face of cloth 200 as it has been partially rolled to a fixed position onto core 205. As soon as it reaches the end of its travel, stop device 208 is raised, ratchet device 209 activated to turn shaft 206 one notch and stop device 208 again locks the position of shaft 206; whereupon the front of the gun 210 is vertically tilted momentarily through an arc to apply cement in a direction further along the cloth to be cemented near to the extremity of the cloth 200, thereby cementing the edge of two compartments. Gun 210, back in its horizontal position, applies ceramic cement back across the face of cloth 200 to the extremity of its travel in the opposite direction. And the sequence repeats at the other end.

It is now seen that, as the matrix is formed it is sealed into the compartments 15a which are closed except towards radial flow therethrough, and that each layer of cloth is laid down onto a layer of ceramic cement which is squeezed between the interstices of the cloth such that it forms a continuous barrier both in forming thereby the radial walls 15b and in sealing the extremities of the cloth. And it is also seen that the inherently high strength of the cloth has been maintained such that it will resist internal pressures exerted upon the walls of any of the compartments. Particularly outstanding is the great hoop strength which allows large pressure differentials between compartments 15a to be easily maintained without rupture, and because the compartment walls 15b are supported by each layer of cloth, they may be relatively quite thin—requiring only that thickness which will ensure against leakage therethrough.

EXAMPLE

A plant for the production of tery-butyl ether (TBE) from methane and isobutane according to the preferred embodiment of the invention operating at about 80 ata pressure (1180 psia) and producing 200,000 metric tons per year of product, or 606 metric tons (about 5450 barrels) per onstream day, uses less than about 6.5 million standard cubic feet per onstream day of methane and less than about 500 and 290 metric tons of isobutane and oxygen, respectively, per onstream day.

No purchased methanol or isobutylene is required, and all of the fuel gas required to power the cryogenic air separation and compress the oxygen is supplied from the process offgases. Over about 91% of the product volume is TBE as methyl TBE, and the rest has value as gasoline. At current U.S. Gulf Coast value for MTBE ($1.30/gal.), the value of the product is over $290,000 per onstream day.

Although in this specification the more preferred means of accomplishing the objects of the invention are described in detail, it will be clear to those skilled in the arts involved that various substitute means may also be employed within the scope of the invention. For example, in respect to the process aspect of the invention, it is clear that, although a rotating regenerator is to be preferred by virtue of the advantages cited, other means of preheating, reacting and quenching, such as fixed bed, switching regenerators, or recuperators may be employed, albeit less advantageously. Thus the invention is not limited except as hereinafter stated in the claims.

I claim:

1. A method for the exothermic partial oxidation of a mixture of hydrocarbonaceous gas and oxygen, which comprises:
   mixing said hydrocarbonaceous gas with a gas comprising oxygen;
   preheating under non-catalytic conditions a first portion of said mixture to a predetermined temperature by heat exchange with product gases from said partial oxidation;
   preheating under non-catalytic conditions a second portion of said mixture to a temperature lower than the temperature of said preheated first portion by heat exchange with product gases from said partial oxidation;
   passing said preheated first portion through a reaction zone; and
   mixing said first portion with said second portion after said first portion has passed through said reaction zone, thereby preventing overheating of said first portion and underheating of said second portion.

2. The method of claim 1, wherein the hydrocarbonaceous gas comprises methane, and product gases from said reaction zone comprise methanol.

3. The method of claim 1, wherein the hydrocarbonaceous gas comprises isobutane, and product gases from said reaction zone comprise isobutylene.

4. The method of claim 3, wherein the hydrocarbonaceous gas comprises methane and isobutane, and product gases from said reaction zone comprise methanol and isobutylene.

5. The method of claim 1, wherein each of said portions is preheated by passing it through heat transfer regenerative means.

6. The method of claim 1, wherein each of said portions is preheated by passing it through a rotary heat transfer regenerator comprising heat storage matrix means.

7. The method of claim 1, wherein each of said portions is preheated by passing it through a rotary heat transfer regenerator having heat storage matrix means comprising glassy ceramic fibers.

8. The method of claim 5, wherein the hydrocarbonaceous gas comprises methane, and product gases from said reaction zone comprise methanol.

9. The method of claim 5, wherein the hydrocarbonaceous gas comprise isobutane, and product gases from said reaction zone comprise isobutylene.

* * * * *